United States Patent
Ubasawa et al.

(10) Patent No.: US 6,767,900 B2
(45) Date of Patent: Jul. 27, 2004

(54) PHOSPHONATE NUCLEOTIDE COMPOUND

(75) Inventors: Masaru Ubasawa, Tokyo (JP); Kouichi Sekiya, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 10/220,126

(22) PCT Filed: Feb. 26, 2001

(86) PCT No.: PCT/JP01/01412
§ 371 (c)(1),
(2), (4) Date: Nov. 4, 2002

(87) PCT Pub. No.: WO01/64693
PCT Pub. Date: Sep. 7, 2001

(65) Prior Publication Data
US 2003/0153534 A1 Aug. 14, 2003

(30) Foreign Application Priority Data
Feb. 29, 2000 (JP) .......................... 2000-054675

(51) Int. Cl.$^7$ .................... C07F 9/6561; A61K 31/675; A61P 31/20; A61P 31/22
(52) U.S. Cl. ........................... 514/81; 544/244
(58) Field of Search ................. 544/244; 514/81

(56) References Cited

U.S. PATENT DOCUMENTS

| 5,840,716 A | 11/1998 | Ubasawa et al. | 514/75 |
| 2003/0109498 A1 * | 6/2003 | Yuasa et al. | 514/81 |

FOREIGN PATENT DOCUMENTS

| EP | 632048 | 1/1995 |
| EP | 785208 | 7/1997 |

* cited by examiner

Primary Examiner—Mark L. Berch
(74) Attorney, Agent, or Firm—Wenderoth, Lind & Ponack, L.L.P.

(57) ABSTRACT

A phosphonate nucleotide compound represented by the following formula (I) or a salt thereof, or a hydrate or solvate thereof:

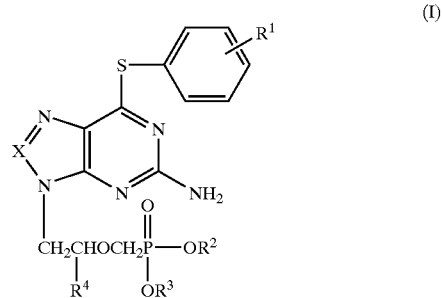

wherein, $R^1$ is a hydroxyl group; each of $R^2$ and $R^3$ is independently a hydrogen atom, a $C_1$–$C_{22}$ alkyl group, an alkanoyloxymethyl group, an alkanoylthioethyl group, or an ethyl group substituted by one or more halogen atoms; $R^4$ is a hydrogen atom, a $C_1$–$C_4$ alkyl group, a $C_1$–$C_4$ hydroxyalkyl group, or a $C_1$–$C_4$ alkyl group substituted by one or more halogen atoms; and X is CH or a nitrogen atom.

13 Claims, No Drawings

PHOSPHONATE NUCLEOTIDE COMPOUND

This application is a 371 of PCT/JP01/01412 filed Feb. 26, 2001.

TECHNICAL FIELD

The present invention relates to a novel phosphonate nucleotide compound. More specifically, the present invention relates to a phosphonate nucleotide compound, salts thereof, and hydrates and solvates thereof, which have an anti-viral activity and are useful as a medicament.

BACKGROUND ART

Infectious viral diseases are recognized as a medically important problem, and for the purpose of treating such diseases, the development of an agent having an anti-viral activity and having no growth inhibiting activity against a normal cell system, has been studied. For example, phosphonate nucleotides are being actively studied as selective anti-viral agents. Specifically, it has been reported that 9-(2-phosphonylmethoxy)ethyladenine (PMEA), 9-(2-phosphonylmethoxy)ethyl-2,6-diaminopurine (PMDAP), and the like are effective against herpes simplex virus type 1 and type 2 (HSV-1 and HSV-2), human immunodeficiency virus (HIV) and human hepatitis B virus (HBV) (Yokota et al., Antimicrob. Agents Chemother., 35, 394 (1991); Votruba et al., Mol. Pharmacol.,32, 524 (1987)).

However, these known phosphonate nucleotide analogues have problems regarding safety, since there is a possibility that they show toxicity such as bone marrow cell growth inhibition and mutagenicity in organisms (Antiviral Research, 16, 77 (1991)). Furthermore, since these compounds do not have oral absorbency (De Clercq et al., Antimicrob. Agents Chemother., 33, 185 (1989)), they have a problem that methods for administration is limited to parenteral administration such as an intravenous injection and an intramuscular injection, in order to obtain a blood level necessary for exerting an effect. Treatment by parenteral administration is difficult for patients other than inpatients, and therefore has not been a preferable treatment for AIDS patients, hepatitis B virus patients and the like who need a long-term treatment.

The present inventors have previously found that certain ester derivatives of phosphonate nucleotide show high oral absorbency (EP632048), and further found an anti-viral agent having no toxicity such as bone marrow cell growth inhibition and mutagenicity by altering a base portion thereof to a specific structure (EP785208). However, such an anti-viral agent is not yet in actual use.

DISCLOSURE OF THE INVENTION

An object of the present invention is to provide an anti-viral agent having no toxicity such as bone marrow cell growth inhibition and mutagenicity. Furthermore, another object of the present invention is to provide a low-cost anti-viral agent obtained by a small number of steps of manufacturing process.

Through intensive studies directed towards the above objects, the present inventors have found that certain 2-amino-6-arylthiopurinephosphonate, which is not specifically disclosed in the aforementioned EP632048 and EP785208, have a high anti-viral activity, and also that these compounds have advantages that they can be synthesized more economically and simply and is more excellent in terms of safety than previously known compounds, thereby completing the present invention.

Thus, the present invention provides a phosphonate nucleotide compound represented by the following formula (I) or a salt thereof, or a hydrate or solvate thereof:

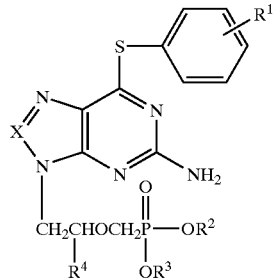

wherein,
R' is a hydroxyl group; each of $R^2$ and $R^3$ is independently a hydrogen atom, a $C_1$–$C_{22}$ alkyl group, an acyloxymethyl group, an acylthioethyl group, or an ethyl group substituted by one or more halogen atoms; $R^4$ is a hydrogen atom, a $C_1$–$C_4$ alkyl group, a $C_1$–$C_4$ hydroxyalkyl group, or a $C_1$–$C_4$ alkyl group substituted by one or more halogen atoms; and X is CH or a nitrogen atom.

Moreover, another aspect of the present invention provides a pharmaceutical composition, which comprises a substance selected from the group consisting of the above compound and salt thereof, and hydrate and solvate thereof, and a pharmacologically acceptable pharmaceutical additive; and an anti-viral agent, which comprises, as an active ingredient, a substance selected from the group consisting of the above compound and salt thereof, and hydrate and solvate thereof. A further aspect of the present invention provides a use of a substance selected from the group consisting of the above compound and salt thereof, and hydrate and solvate thereof for production of the above pharmaceutical composition; and a method for treating virus infection diseases, said method comprising a step of administrating to mammals such as a human, an effective amount of a substance selected from the group consisting of the above compound and salt thereof, and hydrate and a solvate thereof.

THE BEST MODE FOR CARRYING OUT THE INVENTION

The present invention is described in detail below.

In the phosphonate nucleotide compound of the above formula (I), examples of a $C_1$–$C_{22}$ alkyl group represented by $R^2$ and $R^3$ include a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a henicosyl group, and a docosyl group.

Examples of an acyloxymethyl group represented by $R^2$ and $R^3$ include an acetyloxymethyl group, a propionyloxymethyl group, a butyryloxymethyl group, an isobutyryloxymethyl group, a valeryloxymethyl group, an isovaleryloxymethyl group, and a pivaloyloxymethyl group.

Examples of an acylthioethyl group represented by $R^2$ and $R^3$ include an acetylthioethyl group, a propionylthioethyl group, a butyrylthioethyl group, an isobutyrylthioethyl group, a valerylthioethyl group, an isovalerylthioethyl group, and a pivaloylthioethyl group.

In an ethyl group substituted by one or more halogen atoms represented by $R^2$ and $R^3$, the type of the halogen atom may be any of a fluorine, chlorine, bromine or iodine atom. Examples of an ethyl group substituted by one or more halogen atoms include a 1-fluoroethyl group, a 2-fluoroethyl group, a 1-chloroethyl group, a 2-chloroethyl group, a 2-bromoethyl group, a 2,2-difluoroethyl group, a 2,2-dichloroethyl group, a 2,2-dibromoethyl group, a 2,2,2-trifluoroethyl group, a 2,2,2-trichloroethyl group, and a 2,2,2-tribromoethyl group. It is particularly preferable that 2-position of an ethyl group is substituted, and the preferred halogen atom is a fluorine atom. At least one of $R^2$ and $R^3$ is preferably an ethyl group substituted by one or more halogen atoms, particularly preferably a 2,2,2-trifluoroethyl group.

Examples of a $C_1$–$C_4$ alkyl group represented by $R^4$ include a methyl group, an ethyl group, an n-propyl group, an isopropyl group, an n-butyl group, an isobutyl group, a sec-butyl group, and a tert-butyl group. Examples of a $C_1$–$C_4$ hydroxyalkyl group represented by $R^4$ include a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group, and a 4-hydroxybutyl group. Examples of a $C_1$–$C_4$ alkyl group substituted by one or more halogen atoms represented by $R^4$ include a methyl group, an ethyl group, an n-propyl group, an isopropyl group, an n-butyl group, an isobutyl group, a sec-butyl group, and a tert-butyl group to which a halogen atom(s) such as a fluorine atom or a chlorine atom is bound. Specific examples of such groups include a fluoromethyl group, a difluoromethyl group, a trifluoromethyl group, a fluoroethyl group, a chloroethyl group, a fluoropropyl group, a chloropropyl group, a fluorobutyl group, and a chlorobutyl group.

The first condition for the preferred compound of the present invention is that each of $R^2$ and $R^3$ is independently a hydrogen atom, a $C_1$–$C_{22}$ alkyl group, or an ethyl group substituted by one or more halogen atoms. The second condition for the preferred compound of the present invention is that each of $R^2$ and $R^3$ is independently a hydrogen atom, a $C_1$–$C_{22}$ alkyl group or a 2,2,2-trifluoroethyl group, and $R^4$ is a hydrogen atom or a methyl group.

Specific examples of the preferred compounds which satisfy such conditions include the following compounds:

2-amino-9-[2-(phosphonomethoxy)ethyl]-6-(4-hydroxyphenylthio)purine bis(2,2,2-trifluoroethyl) ester;

2-amino-9-[2-(phosphonomethoxy)ethyl]-6-(3-hydroxyphenylthio)purine bis(2,2,2-trifluoroethyl) ester;

2-amino-9-[2-(phosphonomethoxy)ethyl]-6-(2-hydroxyphenylthio)purine bis(2,2,2-trifluoroethyl) ester;

2-amino-9-[2-(phosphonomethoxy)propyl]-6-(4-hydroxyphenylthio)purine bis(2,2,2-trifluoroethyl) ester;

2-amino-9-[2-(phosphonomethoxy)propyl]-6-(3-hydroxyphenylthio)purine bis(2,2,2-trifluoroethyl) ester;

2-amino-9-[2-(phosphonomethoxy)propyl]-6-(2-hydroxyphenylthio)purine bis(2,2,2-trifluoroethyl) ester;

2-amino-9-[2-(phosphonomethoxy)ethyl]-6-(4-hydroxyphenylthio)purine methyl(2,2,2-trifluoroethyl) ester;

2-amino-9-[2-(phosphonomethoxy)ethyl]-6-(3-hydroxyphenylthio)purine methyl(2,2,2-trifluoroethyl) ester;

2-amino-9-[2-(phosphonomethoxy)ethyl]-6-(2-hydroxyphenylthio)purine methyl(2,2,2-trifluoroethyl) ester;

2-amino-9-[2-(phosphonomethoxy)propyl]-6-(4-hydroxyphenylthio)purine methyl(2,2,2-trifluoroethyl) ester;

2-amino-9-[2-(phosphonomethoxy)propyl]-6-(3-hydroxyphenylthio)purine methyl(2,2,2-trifluoroethyl) ester;

2-amino-[2-(phosphonomethoxy)propyl]-6-(2-hydroxyphenylthio)purine methyl(2,2,2-trifluoroethyl) ester;

2-amino-9-[2-(phosphonomethoxy)ethyl]-6-(4-hydroxyphenylthio)purine (2,2,2-trifluoroethyl) ester;

2-amino-9-[2-(phosphonomethoxy)ethyl]-6-(3-hydroxyphenylthio)purine (2,2,2-trifluoroethyl) ester;

2-amino-9-[2-(phosphonomethoxy)ethyl]-6-(2-hydroxyphenylthio)purine (2,2,2-trifluoroethyl) ester;

2-amino-9-[2-(phosphonomethoxy)propyl]-6-(4-hydroxyphenylthio)purine (2,2,2-trifluoroethyl) ester;

2-amino-9-[2-(phosphonomethoxy)propyl]-6-(3-hydroxyphenylthio)purine (2,2,2-trifluoroethyl) ester;

2-amino-9-[2-(phosphonomethoxy)propyl]-6-(2-hydroxyphenylthio)purine (2,2,2-trifluoroethyl) ester;

2-amino-9-[2-(phosphonomethoxy)ethyl]-6-(4-hydroxyphenylthio)purine;

2-amino-9-[2-(phosphonomethoxy)ethyl]-6-(3-hydroxyphenylthio)purine;

2-amino-9-[2-(phosphonomethoxy)ethyl]-6-(2-hydroxyphenylthio)purine;

2-amino-9-[2-(phosphonomethoxy)propyl]-6-(4-hydroxyphenylthio)purine;

2-amino-9-[2-(phosphonomethoxy)propyl]-6-(3-hydroxyphenylthio)purine; and 2-amino-9-[2-(phosphonomethoxy)propyl]-6-(2-hydroxyphenylthio)purine.

The third condition for the preferred compound of the present invention is that each of $R^2$ and $R^3$ is a 2,2,2-trifluoroethyl group and $R^4$ is a hydrogen atom or a methyl group. Examples of preferred compounds which satisfy such conditions include the following compounds:

2-amino-9-[2-(phosphonomethoxy)ethyl]-6-(4-hydroxyphenylthio)purine bis(2,2,2-trifluoroethyl) ester;

2-amino-9-[2-(phosphonomethoxy)ethyl]-6-(3-hydroxyphenylthio)purine bis(2,2,2-trifluoroethyl) ester;

2-amino-9-[2-(phosphonomethoxy)ethyl]-6-(2-hydroxyphenylthio)purine bis(2,2,2-trifluoroethyl) ester;

2-amino-9-[2-(phosphonomethoxy)propyl]-6-(4-hydroxyphenylthio)purine bis(2,2,2-trifluoroethyl) ester;

2-amino-9-[2-(phosphonomethoxy)propyl]-6-(3-hydroxyphenylthio)purine bis(2,2,2-trifluoroethyl) ester; and 2-amino-9-[2-(phosphonomethoxy)propyl]-6-(2-hydroxyphenylthio)purine bis(2,2,2-trifluoroethyl) ester.

The fourth condition for the preferred compound of the present invention is that $R^1$ is a hydroxyl group, each of $R^2$ and $R^3$ is a 2,2,2-trifluoroethyl group, and $R^4$ is a hydrogen atom. Examples of preferred compounds which satisfy such conditions include the following compounds:

2-amino-9-[2-(phosphonomethoxy)ethyl]-6-(4-hydroxyphenylthio)purine bis(2,2,2-trifluoroethyl) ester;

2-amino-9-[2-(phosphonomethoxy)ethyl]-6-(3-hydroxyphenylthio)purine bis(2,2,2-trifluoroethyl) ester; and 2-amino-9-[2-(phosphonomethoxy)ethyl]-6-(2-hydroxyphenylthio)purine bis(2,2,2-trifluoroethyl) ester.

The phosphonate nucleotide compound of the formula (I) of the present invention may exist as a salt, and any salt formed by the above compound falls within the scope of the present invention. Examples of such a salt include a pharmaceutically acceptable salt. Where an acidic group exists, the acidic group is able to form metal salts such as a lithium salt, a sodium salt, a potassium salt, a magnesium salt and a calcium salt, and ammonium salts such as an ammonium salt, a methyl ammonium salt, a dimethyl ammonium salt, a trimethyl ammonium salt and dicyclohexyl ammonium salt. Where an amino group exists, the amino group is able to form mineral acid salts such as hydrochloride, hydrobromide, sulfate, nitrate, phosphate and metaphosphate, and organic acid salts such as methanesulfonate, benzenesulfonate, para-toluenesulfonate, acetate, propionate, tartrate, fumarate, maleate, malate, oxalate, succinate, citrate, benzoate, mandelate, cinnamate, lactate, besylate, valerate, stearate, oleate, lactobionate, ethylsuccinate, semisuccinate, butyrate, palmitate, carbamate, gluconate, laurate, salicylate, laokurate, tannate and butylsulfonate.

The phosphonate nucleotide compound of the formula (I) of the present invention and salt thereof may exist in the form of a hydrate or solvate. Any hydrate or solvate, which is formed by the phosphonate nucleotide compound of the formula (I) of the present invention or salt thereof, including preferred compounds specifically referred to above, falls within the scope of the present invention. Examples of a solvent capable of forming the solvate include methanol, ethanol, isopropanol, acetone, ethyl acetate, methylene chloride, and diisopropyl ether.

Specific examples of the compounds of the present invention are shown in Table 1 (wherein Me- represents a methyl group, Et- represents an ethyl group, i-Pr-represents an isopropyl group, and t-Bu- represents a tert-butyl group).

TABLE 1

| No. | $R^1$ | $R^2$ | $R^3$ | $R^4$ | X |
|---|---|---|---|---|---|
| 1 | 2-OH | $CF_3CH_2$— | $CF_3CH_2$— | H | CH |
| 2 | 3-OH | $CF_3CH_2$— | $CF_3CH_2$— | H | CH |
| 3 | 4-OH | $CF_3CH_2$— | $CF_3CH_2$— | H | CH |
| 4 | 2-OH | $CF_3CH_2$— | $CF_3CH_2$— | H | N |
| 5 | 3-OH | $CF_3CH_2$— | $CF_3CH_2$— | H | N |
| 6 | 4-OH | $CF_3CH_2$— | $CF_3CH_2$— | H | N |
| 7 | 2-OH | $CF_3CH_2$— | Me— | H | CH |
| 8 | 3-OH | $CF_3CH_2$— | Me— | H | CH |
| 9 | 4-OH | $CF_3CH_2$— | Me— | H | CH |
| 10 | 2-OH | $CF_3CH_2$— | Me— | H | N |
| 11 | 3-OH | $CF_3CH_2$— | Me— | H | N |
| 12 | 4-OH | $CF_3CH_2$— | Me— | H | N |
| 13 | 2-OH | $CF_3CH_2$— | Et— | H | CH |
| 14 | 3-OH | $CF_3CH_2$— | Et— | H | CH |
| 15 | 4-OH | $CF_3CH_2$— | Et— | H | CH |
| 16 | 2-OH | $CF_3CH_2$— | H | H | CH |
| 17 | 3-OH | $CF_3CH_2$— | H | H | CH |
| 18 | 4-OH | $CF_3CH_2$— | H | H | CH |
| 19 | 2-OH | $CF_3CH_2$— | H | H | N |
| 20 | 3-OH | $CF_3CH_2$— | H | H | N |
| 21 | 4-OH | $CF_3CH_2$— | H | H | N |
| 22 | 2-OH | H | H | H | CH |
| 23 | 3-OH | H | H | H | CH |
| 24 | 4-OH | H | H | H | CH |
| 25 | 2-OH | H | H | H | N |
| 26 | 3-OH | H | H | H | N |
| 27 | 4-OH | H | H | H | N |
| 28 | 2-OH | $CF_3CH_2$— | $CF_3CH_2$— | Me— | CH |
| 29 | 3-OH | $CF_3CH_2$— | $CF_3CH_2$— | Me— | CH |
| 30 | 4-OH | $CF_3CH_2$— | $CF_3CH_2$— | Me— | CH |
| 31 | 2-OH | $CF_3CH_2$— | $CF_3CH_2$— | Me— | N |
| 32 | 3-OH | $CF_3CH_2$— | $CF_3CH_2$— | Me— | N |
| 33 | 4-OH | $CF_3CH_2$— | $CF_3CH_2$— | Me— | N |
| 34 | 2-OH | $CF_3CH_2$— | Me— | Me— | CH |
| 35 | 3-OH | $CF_3CH_2$— | Me— | Me— | CH |
| 36 | 4-OH | $CF_3CH_2$— | Me— | Me— | CH |
| 37 | 2-OH | $CF_3CH_2$— | Me— | Me— | N |
| 38 | 3-OH | $CF_3CH_2$— | Me— | Me— | N |
| 39 | 4-OH | $CF_3CH_2$— | Me— | Me— | N |
| 40 | 2-OH | $CF_3CH_2$— | Et— | Me— | CH |
| 41 | 3-OH | $CF_3CH_2$— | Et— | Me— | CH |
| 42 | 4-OH | $CF_3CH_2$— | Et— | Me— | CH |
| 43 | 2-OH | $CF_3CH_2$— | Et— | Me— | N |
| 44 | 3-OH | $CF_3CH_2$— | Et— | Me— | N |
| 45 | 4-OH | $CF_3CH_2$— | Et— | Me— | N |
| 46 | 2-OH | $CF_3CH_2$— | H | Me— | CH |
| 47 | 3-OH | $CF_3CH_2$— | H | Me— | CH |
| 48 | 4-OH | $CF_3CH_2$— | H | Me— | CH |
| 49 | 2-OH | $CF_3CH_2$— | H | Me— | N |
| 50 | 3-OH | $CF_3CH_2$— | H | Me— | N |
| 51 | 4-OH | $CF_3CH_2$— | H | Me— | N |
| 52 | 2-OH | H | H | Me— | CH |
| 53 | 3-OH | H | H | Me— | CH |

TABLE 1-continued

| No. | $R^1$ | $R^2$ | $R^3$ | $R^4$ | X |
|---|---|---|---|---|---|
| 54 | 4-OH | H | H | Me— | CH |
| 55 | 2-OH | H | H | Me— | N |
| 56 | 3-OH | H | H | Me— | N |
| 57 | 4-OH | H | H | Me— | N |
| 58 | 2-OH | —CH$_2$O—CO—t-Bu | —CH$_2$O—CO—t-Bu | H | CH |
| 59 | 3-OH | —CH$_2$O—CO—t-Bu | —CH$_2$O—CO—t-Bu | H | CH |
| 60 | 4-OH | —CH$_2$O—CO—t-Bu | —CH$_2$O—CO—t-Bu | H | CH |
| 61 | 2-OH | —CH$_2$O—CO—t-Bu | —CH$_2$O—CO—t-Bu | Me— | CH |
| 62 | 3-OH | —CH$_2$O—CO—t-Bu | —CH$_2$O—CO—t-Bu | Me— | CH |
| 63 | 4-OH | —CH$_2$O—CO—t-Bu | —CH$_2$O—CO—t-Bu | Me— | CH |
| 64 | 2-OH | —CH$_2$CH$_2$S—CO—i-Pr | —CH$_2$CH$_2$S—CO—i-Pr | H | CH |
| 65 | 3-OH | —CH$_2$CH$_2$S—CO—i-Pr | —CH$_2$CH$_2$S—CO—I—Pr | H | CH |
| 66 | 4-OH | —CH$_2$CH$_2$S—CO—i-Pr | —CH$_2$CH$_2$S—CO—I—Pr | H | CH |
| 67 | 2-OH | —CH$_2$CH$_2$S—CO—i-Pr | —CH$_2$CH$_2$S—CO—I—Pr | Me— | CH |
| 68 | 3-OH | —CH$_2$CH$_2$S—CO—i-Pr | —CH$_2$CH$_2$S—CO—I—Pr | Me— | CH |
| 69 | 4-OH | —CH$_2$CH$_2$S—CO—i-Pr | —CH$_2$CH$_2$S—CO—I—Pr | Me— | CH |

As a production method of the compound of the present invention in the case where in the formula (I), each of $R^2$ and $R^3$ is a $C_1$–$C_{22}$ alkyl group, or an ethyl group substituted by one or more halogen atoms, the compound can be synthesized, for example, according to the following reaction route (1) or (2). In the following scheme, $R^1$, $R^4$ and X are the same as defined above, $R^5$ represents a $C_1$–$C_{22}$ alkyl group, or an ethyl group substituted by one or more halogen atoms, and W represents a leaving group such as a halogen atom, a para-toluenesulfonyloxy group, a methanesulfonyloxy group or a trifluoromethanesulfonyloxy group.

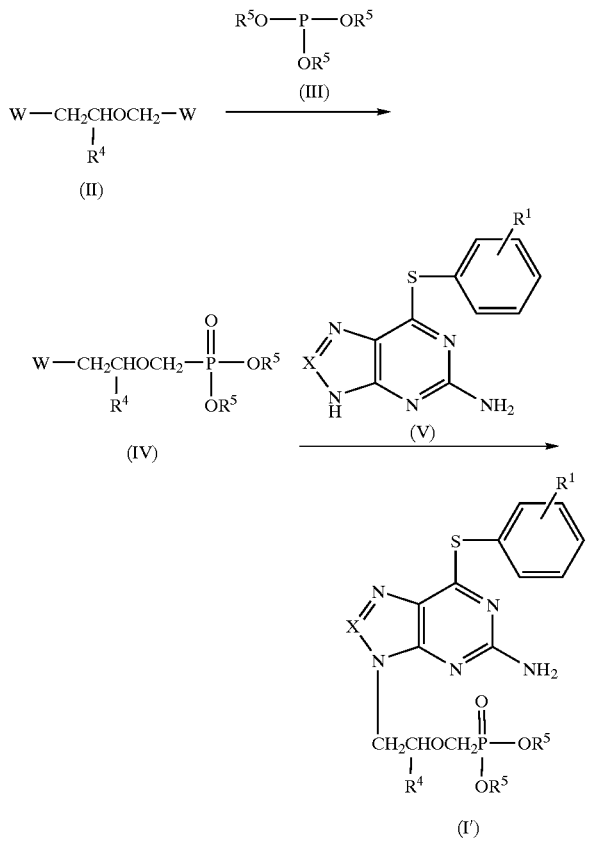

First, the compound of the above formula (II) is reacted with the compound of the above formula (III) at a temperature of 10° C. to 250° C., preferably 130° C. to 200° C., for 0.1 to 100 hours, preferably for 3 to 24 hours. The compound of the above formula (IV) obtained by the above reaction can be separated and purified by ordinary separation and purification means such as distillation-, adsorption- or partition-chromatographies, as necessary. The compound of the above formula (IV) may be separated and purified as stated above, or it may directly be used for the following reaction without purification. That is, the compound of the above formula (IV) is reacted with the compound of the above formula (V) in the presence of a base such as sodium carbonate, potassium carbonate, cesium carbonate, sodium hydrate, potassium hydrate, triethylamine and diazabicycloundecen in a suitable solvent such as acetonitrile, tetrahydrofuran, dimethylsulfoxide, dimethylformamide or methylpyrrolidone at a temperature of 10° C. to 200° C., preferably 50° C. to 150° C., for 0.1 to 100 hours, preferably for 1 to 10 hours, to obtain the compound of the above formula (I').

The source of the compounds of the above formulas (II), (III) and (V) which are raw materials for reaction route (1) is not particularly limited. For example, a compound commercially available as a reagent may be used, or a compound may be synthesized by a known method, as appropriate. By way of example, the compound of the above formula (V) can be synthesized by heating the compound of the formula (VI) and the compound of the formula (VIII) which are described later, in a suitable solvent such as acetonitrile or dimethylsulfoxide at a range of 50° C. to 100° C.

The compound of the above formula (I') can also be produced by the following method. In the following scheme, $R^1$, $R^4$, $R^5$, X and W are the same as defined above.

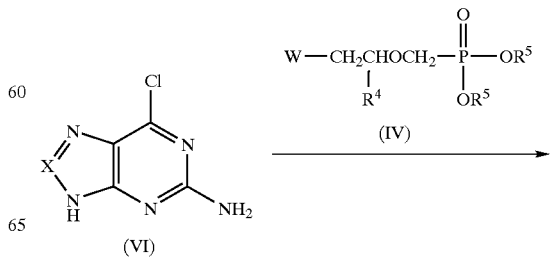

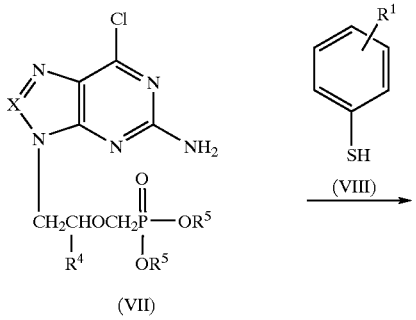

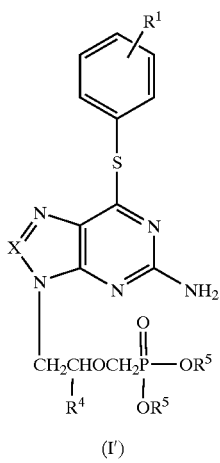

The compound of the above formula (IV) obtained by reaction route (1) is reacted with the compound of the above formula (VI) in the presence of a base such as sodium carbonate, potassium carbonate, cesium carbonate, sodium hydrate, potassium hydrate, triethylamine and diazabicycloundecen in a suitable solvent such as acetonitrile, tetrahydrofuran, dimethylsulfoxide, dimethylformamide or methylpyrrolidone at a temperature of 10° C. to 200° C., preferably 50° C. to 150° C. for 0.1 to 100 hours, preferably for 0.5 to 10 hours, to obtain the compound of the above formula (VII). Thereafter, the compound of the above formula (VII) is reacted with a mercaptan represented by the above formula (VIII) or a salt thereof such as a sodium salt, a potassium salt, a lithium salt or a triethylamine salt, in a suitable solvent such as acetonitrile, tetrahydrofuran, dimethylsulfoxide, dimethylformamide or methylpyrrolidone optionally in the presence of a suitable tertiary amine at a temperature of 10° C. to 200° C., preferably 70° C. to 120° C. for 0.1 to 100 hours, preferably for 0.5 to 12 hours, to obtain the compound of the above formula (I'). The compound of the formula (I') corresponds to a compound of the formula (I) wherein each of $R^2$ and $R^3$ is a $C_1$–$C_{22}$ alkyl group, or an ethyl group substituted by one or more halogen atoms. The source of the compound of the above formula (VI) which is a raw material of reaction route (2), is not particularly limited. For example, a compound commercially available as a reagent may be used, or the compound may be synthesized by a known method as appropriate.

By further altering a phosphate ester portion of the compound of the above formula (I'), there can be obtained the compound of the formula (I) wherein $R^5$ of the compound of the formula (I') is converted into another substituent. For example, a compound of the formula (I) wherein both $R^2$ and $R^3$ are hydrogen atoms can be obtained by hydrolysis of the compound of the above formula (I'). Moreover, a compound of the formula (I) wherein $R^3$ is a hydrogen atom, a $C_1$–$C_{22}$ alkyl group, an acylthioethyl group, or an ethyl group substituted by one or more halogen atoms, and $R^2$ is a $C_1$–$C_{22}$ alkyl group, or an ethyl group substituted by one or more halogen atoms, can be obtained by reaction of the compound of the above formula (I') with the compound of the formula (IX): $R^6$OH wherein $R^6$ is a hydrogen atom, a $C_1$–$C_{22}$ alkyl group, an acylthioethyl group, or an ethyl group substituted by one or more halogen atoms, in no solvent or in a suitable solvent including a chloric solvent such as dichloromethane; pyridine; acetonitrile; tetrahydrofuran; dimethylsulfoxide; dimethylformamide and methylpyrrolidone, optionally in the presence of acid or alkali, at a temperature of 10° C. to 100° C., preferably 20° C. to 30° C., for 0.1 to 100 hours, preferably 5 to 12 hours.

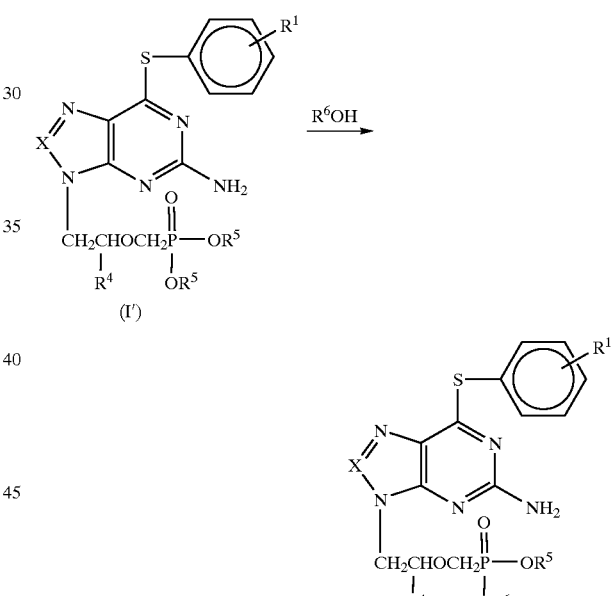

In the above scheme, $R^1$, $R^4$, $R^5$, $R^6$ and X are the same as defined above.

A compound of the formula (I) wherein each of $R^2$ and $R^3$ is independently a hydrogen atom, a $C_1$–$C_{22}$ alkyl group, an acylthioethyl group, or an ethyl group substituted by one or more halogen atoms, can also be obtained by the following method In the following scheme, $R^1$, $R^4$ and X are the same as defined above, and each of $R^7$ and $R^8$ is independently a hydrogen atom, a $C_1$–$C_{22}$ alkyl group, an acylthioethyl group, or an ethyl group substituted by one or more halogen atoms, with the exception that both $R^7$ and $R^8$ can not represent hydrogen atoms at the same time.

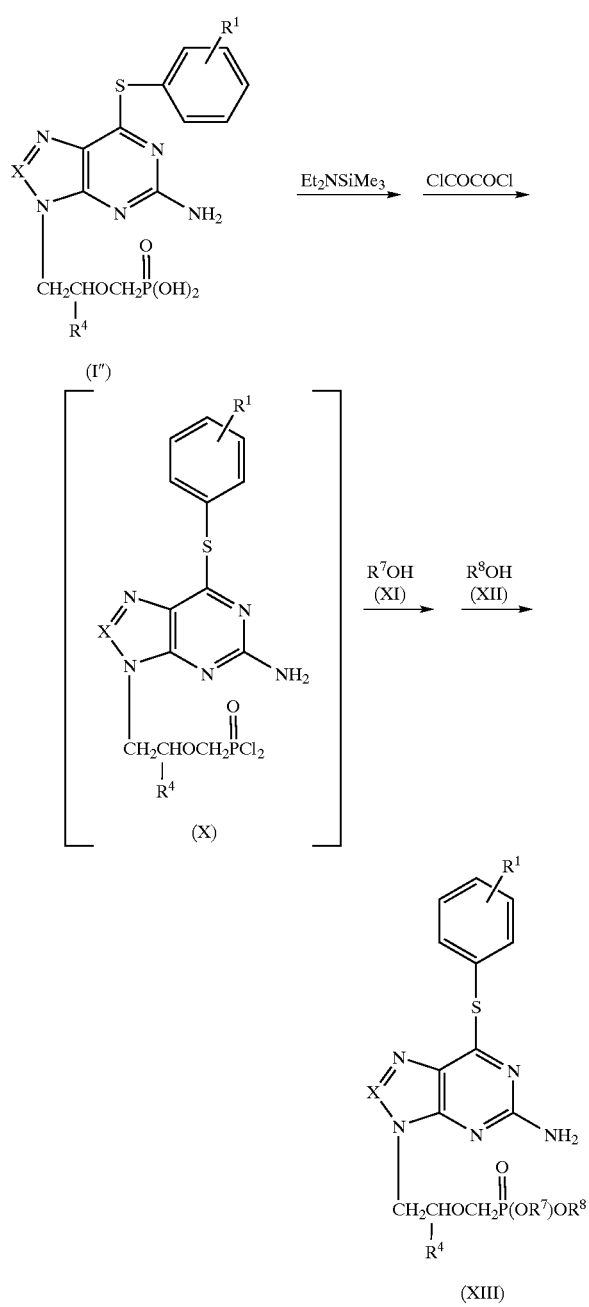

First, the compound of the above formula (I") is reacted with trimethylsilyldiethylamine in a suitable solvent such as dichloromethane, dichloroethane and chloroform around room temperature for about 1 hour. More than two moles of trimethylsilyldiethylamine are used per mole of the compound of the above formula (I"). After the reaction solution is concentrated to dryness, the residue is dissolved into a suitable solvent, for example, a chloric solvent such as dichloromethane, and then oxalyl chloride is added in an amount of 2 or more moles per mole of the compound of the above formula (I"), followed by reaction on ice for about 1 hour, and then around room temperature for about 1 hour in the presence of a catalytic amount of dimethylformamide.

The compound of the above formula (X) obtained by removal of the solvent, usually without being purified, is reacted with the compound of the formula (XI) and/or the compound of the formula (XII) in a suitable solvent, for example, a chloric solvent such as dichloromethane, pyridine, acetonitrile, tetrahydrofuran, dimethylsulfoxide, dimethylformamide or methylpyrrolidone, at a temperature of 10° C. to 100° C., preferably 20° C. to 30° C. for 0.1 to 100 hours, preferably 5 to 12 hours. The obtained compound of the formula (XIII) corresponds to a compound of the formula (I) wherein each of $R^2$ and $R^3$ is independently a hydrogen atom, a $C_1$–$C_{22}$ alkyl group, an acylthioethyl group, or an ethyl group substituted by one or more halogen atoms with the exception that both $R^2$ and $R^3$ can not represent hydrogen atoms at the same time. As stated above, the compound of the above formula (I") which is a raw material of the above reaction, can be obtained by hydrolysis of the compound of the formula (I'), or it can be more efficiently obtained by reaction of a compound of the formula (I') wherein $R^5$ is a $C_1$–$C_{22}$ alkyl group with triethyliodosilane, trimethylbromosilane and the like.

A compound of the formula (I) wherein each of $R^2$ and $R^3$ is an acyloxymethyl group, or wherein either one of $R^2$ and $R^3$ is an acyloxymethyl group and the other is hydrogen, can be obtained by reaction of the compound of the above formula (I") with an acyloxymethyl halide represented by the following formula (XIV): $R^9Y$ wherein $R^9$ is an acyloxymethyl group and Y is a chlorine, bromine or iodine atom, in the presence of a base such as sodium carbonate, potassium carbonate, cesium carbonate, sodium hydride, potassium hydride, triethylamine, pyridine, diazabicycloundecen and N,N'-dichlorohexyl-4-morpholinecarboxamidine in a suitable solvent such as acetonitrile, tetrahydrofuran, dimethylsulfoxide, dimethylformiamide or methylpyrrolidone at a temperature of 0° C. to 200° C., preferably 10° C. to 100° C. for 1 to 300 hours, preferably for 10 to 200 hours. In the case of a compound wherein each of $R^2$ and $R^3$ is an acyloxymethyl group, the compound of the formula (XIV) may be reacted with the compound of the formula (I") in an amount of 2 moles per mole of the compound of the formula (I"), while in the case of a compound wherein either one is an acyloxymethyl group, an equivalent mole reaction may be applied.

A compound wherein either one of $R^2$ and $R^3$ is an acyloxymethyl group, and the other is a $C_1$–$C_{22}$ alkyl group, an acylthioethyl group, or an ethyl group substituted by one or more halogen atoms, can be produced by preparing a compound wherein either one of $R^2$ and $R^3$ is a $C_1$–$C_{22}$ alkyl group, an acylthioethyl, group or an ethyl group substituted by one or more halogen atoms, and the other is a hydrogen atom, and then reacting the compound of the above formula (XIV) to this compound by the above method.

Regarding thiophenol derivatives (the compound of the formula (VIII)) which are used in the production methods stated above, alkoxy-substituted thiophenols exemplified in EP632048 is synthesized through several processes (3 processes) from commercially available hydroxy-substituted thiophenol, so that the number of the steps of manufacturing process is increased, thereby greatly influencing the cost of synthesis. In comparison with this, where the compound of the present invention is produced, a commercially available hydroxy-substituted thiophenol is directly used in the following manufacturing process steps. Thus, to obtain the compound described in EP632048, additional 3 steps of manufacturing process are necessary, as compared to the case where the compound of the present invention is obtained. The increase of the steps of manufacturing process exerts a great influence upon the cost of synthesis. Therefore, according to the present invention, a low-cost medicament is provided by a reduction of the cost of synthesis.

The salt of the compound of the formula (I) can be synthesized, for example, by the following method. The compound of the formula (I') is reacted with a corresponding acid with stirring at a temperature of −10° C. to 100° C., preferably 10° C. to 50° C. for 0.1 to 20 hours, preferably for 0.3 to 1 hour in a suitable solvent such as ethyl acetate, isopropanol, acetonitrile, tetrahydrofuran, dimethylsulfoxide, dimethylformamide or methylpyrrolidone.

The above stated production method is provided as an example of a method for producing the compound of the formula (I) of the present invention, and the method for producing the compound of the present invention is not limited thereto. Since a method for producing the compound of the present invention is described more specifically in the examples of the present specification, a person skilled in the art can produce compounds which are included in the above formula (I) according to the above stated general descriptions and the specific descriptions in the examples, with addition of appropriate alterations and modifications thereto as required. The compound of the above formula (I) produced by the above method or a salt thereof can be separated and purified by ordinary nucleotide separation and purification means, e.g., by selecting and applying means such as recrystallization-, adsorption-, ion exchange- and partition-chromatographies, as appropriate.

The compound of the present invention is useful as an active ingredient for a medicament, and specifically it is useful as an active ingredient of an anti-viral agent as shown in test examples described hereinafter. Moreover, the compound of the present invention is expected to have anti-tumoral activity as shown by other ionic phosphonate nucleotide analogues. A target virus to which the medicament of the present invention is applicable is not particularly limited, and specific examples of the virus include an RNA virus such as human immunodeficiency virus, influenza virus and hepatitis C virus; and a DNA virus such as herpes simplex virus type 1, herpes simplex virus type 2, cytomegalovirus, varicella-zoster virus and hepatitis B virus, with hepatitis B virus being more preferable.

Where the compound of the present invention is used as a medicament, it may be used singly, but it is preferred that, using a pharmacologically acceptable pharmaceutical additive, a pharmaceutical composition comprising the above compound as an active ingredient is produced and administered. The composition of the pharmaceutical composition is determined by the solubility of the compound, chemical properties, administration route, dosage regimen and the like. For example, the compound of the present invention can be orally administered in an dosage form of a granule, a parvule, a powder, a tablet, a hard syrup, a soft capsule, a troche, a syrup, an emulsion, a soft gelatine capsule, a gel, a paste, a suspension, a liposome and the like, or the compound can be administered intravenously, intramuscularly or subcutaneously in the form of an injection. In addition, the compound of the present invention may be formulated into powders for injection, and a solution may be prepared before use.

As a pharmacologically acceptable pharmaceutical additive, an organic or inorganic, solid or liquid carrier, which is suitable for oral, enteral, parenteral or local administration, can be used. Examples of a solid carrier used for the production of a solid formulation include lactose, sucrose, starch, talc, cellulose, dextrin, kaoline, calcium carbonate, agar, pectin, stearic acid, magnesium stearate, lecithin, and sodium chloride. Examples of a liquid carrier used for the production of a liquid formulation for oral administration include glycerine, peanut oil, polyvinylpyrrolidone, olive oil, ethanol, benzyl alcohol, propylene glycol, physiological saline, and water. The above pharmaceutical composition can also comprise, in addition to the above carriers, an adjuvant such as a wetting agent, a suspension aid, a sweetener, a flavor, a coloring agent and a preservative. Further, a liquid agent may be contained in a capsule of a substance which can be absorbed, such as gelatin. Examples of a solvent or a suspending agent, which is used for the production of a formulation for parenteral administration such as an injection, include water, propylene glycol, polyethylene glycol, benzyl alcohol, ethyl oleate, and lecithin.

Considering the properties of known compounds, it can easily be assumed that the compound of the present invention, especially the ester derivative of the above formula (I') has a high oral absorbency, and therefore oral administration is a preferred administration route for the medicament of the present invention. The preparation of each of the above formulation can be carried out according to standard techniques. Where the medicament of the present invention is used for oral administration, the clinical dose is generally 0.1 to 500 mg of the compound per kg adult per day, and preferably 1 to 50 mg of the compound per kg adult per day. The dose may be changed as appropriate, depending on age, disease condition, symptom, the presence or absence of concurrent administration and the like. The above dose may be applied once a day or divided over two to several administrations per day at regular intervals, or may also be applied intermittently every several days. Where the compound of the present invention is used as an injection, the applied dose is 0.01 to 50 mg of the compound per kg adult per day, preferably 0.1 to 5 mg per kg.

EXAMPLES

The present invention is further described in the following examples. The present invention is not limited to the Examples so song as it does not go beyond the gist of the invention. The compound numbers in the Examples correspond to those in Table 1.

Example 1

Production of 2-amino-9-[2-(phosphonomethoxy)ethyl]-6-(4-hydroxyphenylthio)purine bis(2,2,2-trifluoroethyl) ester (Compound No. 3)

87 g of 2-chloroethyl chloromethyl ether (670 mmol) was reacted with 200 g of Tris(2,2,2-trifluoroethyl)phosphite (610 mmol) at 160° C. for 7 hours to obtain 2-[bis(2,2,2-trifluoroethyl)phosphonylmethoxy]ethyl chloride quantitatively.

206 g of 2-(phosphonomethoxy)ethyl chloride bis(2,2,2-trifluoroethyl) ester was dissolved in 2,000 ml of methyl ethyl ketone, 270 g of sodium iodide was added thereto, and the mixture was refluxed for 8 hours. After reaction, the mixture was cooled to room temperature followed by concentration to dryness. The residue was dissolved in chloroform/hexane and then was adsorbed to a silica gel column, followed by elution with chloroform/hexane to obtain 2-(phosphonomethoxy)ethyl iodide bis (2,2,2-trifluoroethyl) ester quantitatively.

15.0 g (88 mmol) of 2-amino-6-chloropurine was suspended in 360 ml of dimethylformamide, and the suspension was reacted with 13.9 ml (93 mmol) of 1,8-diazabicyclo [5.4.0]undec-7-ene at 80° C. for 1 hour. 23.8 ml of 2-(phosphonomethoxy)ethyl iodide bis(2,2,2-trifluoroethyl) ester was added to the above reaction solution, and the mixture was reacted at 100° C. for 5 hours. After reaction, the mixture was cooled to room temperature, followed by concentration to dryness. The residue was dissolved in chloroform, and was then adsorbed to a silica gel column followed by elution with 5%-methanol-chloroform to obtain 23.3 g (yield 56%) of 2-amino-9-[2-(phosphonomethoxy) ethyl]-6-chloropurine bis(2,2,2-trifluoroethyl) ester.

To 10 ml of dimethylformamide solution containing 2 g of 2-amino-9-[2-(phosphonomethoxy)ethyl]-6-chloropurine bis(2,2,2-trifluoroethyl) ester, 0.8 ml of pyridine and 0.64 g of 4-hydroxythiophenol were added, and the mixture was stirred at 100° C. for 2 hours. The reaction mixture was cooled to room temperature followed by concentration to dryness. The residue was dissolved in chloroform and was then adsorbed to a silica gel column followed by elution with 5% to 20% methanol-chloroform to obtain 1.3 g (yield 55%) of 2-amino-9-[2-(phosphonomethoxy) ethyl]-6-(4-hydroxyphenylthio)purine bis(2,2,2-trifluoroethyl) ester.

$^1$H-NMR (DMSO-d6, δ):3.85–3.88 (m, 2H), 4.14 (d, J=8.1 Hz, 2H), 4.19–4.22 (m, 2H), 4.62–4.71 (m, 4H), 6.27 (s, 2H), 6.84 (d, J=8.7 Hz, 2H) 7.7 (d, J=8.7 Hz, 2H), 7.89 (s, 1H), 9.85 (s, 1H)

Example 2

Production of 2-amino-9-[2-(phosphonomethoxy)ethyl]-6-(4-hydroxyphenylthio)purine methyl(2,2,2-trifluoroethyl) ester (Compound No. 9)

100 mg of 2-amino-9-[2-(phosphonomethoxy)ethyl]-6-(4-hydroxyphenylthio) purine bis(2,2,2-trifluoroethyl) ester (Compound No. 3) was dissolved in a 0.35N ammonia methanol solution, and the mixture was left at room temperature for 40 minutes, followed by removal of the solvent by distillation to obtain the compound of interest.

$^1$H-NMR (DMSO-d6, δ):3.66 (d, J=4.5 Hz, 3H), 3.83–3.87 (m, 2H), 4.00 (d, J=8.1 Hz, 2H), 4.18–4.22 (m, 2H), 4.52–4.60 (m, 2H), 6.23 (s, 2H), 6.83 (d, j=8.4 Hz, 2H), 7.37 (d, J=8.4 Hz, 2H), 7.89 (s, 1H), 9.81 (s, 1H)

Example 3

Production of 2-amino-9-[2-(phosphonomethoxy)ethyl]-6-(4-hydroxyphenylthio)purine 2,2,2-trifluoroethyl ester (Compound No. 18)

60 mg of 2-amino-9-[2-(phosphonomethoxy)ethyl]-6-(4-hydroxyphenylthio)purine bis(2,2,2-trifluoroethyl) ester (Compound No. 3) was dissolved in a 1N ammonia solution, and the mixture was left at room temperature for 3 hours, followed by removal of the solvent by distillation to obtain the compound of interest.

$^1$H-NMR (DMSO-d6, δ):3.51–3.54 (m, 2H), 3.74–3.77 (m, 2H), 4.03–4.12 (m, 2H), 4.14–4.16 (m, 2H), 6.20 (s, 2H), 6.82 (d, J=8.4 Hz, 2H), 7.12 (b, 3H), 7.36 (d, j=8.4 Hz, 2), 8.00 (s, 1 H), 9.81 (s, 1 H)

Example 4

Production of 2-amino-9-[2-(phosphonomethoxy)ethyl]-6-(4-hydroxyphenylthio)purine (Compound No. 24)

2-amino-9-[2-(phosphonomethoxy)ethyl]-6-chloropurine bisisopropyl ester was obtained by the same process as in Example 1, with the exception that triisopropylphosphite was used instead of tris(2,2,2-trifluoroethyl)phosphite.

4.1 ml of bromotrimethylsilane was added to 37 ml of acetonitrile solution containing 3.7 g of 2-amino-9-[2-(phosphonomethoxy)ethyl]-6-chloropurine bisisopropyl ester, and the mixture was stirred at 25° C. for 16 hours. Thereafter, the solvent was removed under vacuum and the residue was crystallized from 45 ml of acetone/15 ml of water to obtain 2.4 g of 2-amino-9-[2-(phosphonomethoxy) ethyl]-6-chloropurine. 304 mg of 4-hydroxythiophenol and 0.32 ml of pyridine were added to 5 ml of DMF solution containing 308 mg of the above-obtained compound, and the mixture was heated at 100° C. for 4 hours. After removal of the solvent by distillation, the compound of interest was isolated by high performance liquid chromatography.

$^1$H-NMR (DMSO-d6, δ):3.57–3.60 (m, 2H), 3.81–3.84 (m, 2H), 6.83 (d, J=8.7 Hz, 2H), 7.38 (d, J=8.7 Hz, 2H), 7.96 (s, 1H)

Test Example 1

Inhibitory Effect Against Growth of Hepatitis B Virus (HBV)

The inhibitory effect of the compound of the present invention against the growth of an HBV was measured by a known method (K. Ueda, et al., Virology, 169, 213–216 (1989)). $2 \times 10^4$ of HB611 cells (recombinant human hepatoma cells producing HBV) were cultured at 37° C. in Dulbecco ME medium containing 10% fetal bovine serum, streptomycin (100 μg/ml), penicillin (100IU/ml) and Genetisin (trade name, antibiotic by LifeTechnologies) (0.2 mg/ml). At the second day and the fifth day of culturing, the medium was replaced by a fresh medium, and then at the eighth day, the eleventh day and the fourteenth day of culturing, the medium was replaced with a medium containing 0.005 to 100 μM (final concentration) of the test compound, and at the seventeenth day of culturing, DNA of the cells were collected. HBV-DNA amount contained in the cells was determined by Southern blotting, and 50% inhibition concentration against HBV-DNA synthesis in the cells was determined. Moreover, a concentration of the compounds required to kill 50% of HB611 cells was determined. The results are shown in Table 2.

Each compound number in the table corresponds to the compound number in Table 1. For reference, the results of the evaluation of the compounds described in EP785208 are also shown.

As shown in Table 2, Compound No. 3 of the present application shows an activity equivalent to the compounds of the Reference Examples that have a similar structure (bis(2,2,2-trifluoroethyl) ester) described in EP785208.

TABLE 2

| Test compound | 50% inhibition concentration against HBV-DNA synthesis (μM) | Cytotoxic concentration required to kill 50% of HB611 cells (μM) |
| --- | --- | --- |
| Compound No. 3 | 0.05 | >1,000 |
| Reference Example 1 ($R^1$ = 2-OMe in A) | 0.08 | >1,000 |
| Reference Example 2 ($R^1$ = 3-OMe in A) | 0.04 | >1,000 |
| Reference Example 3 ($R^1$ = 4-OMe in A) | 0.05 | >1,000 |

Compound of Reference Example

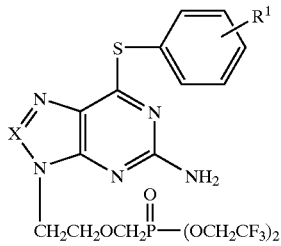

A

INDUSTRIAL APPLICABILITY

The phosphonate nucleotide compound of the present invention has an excellent anti-viral activity, as well as a high oral absorbency and high safety for organisms. Furthermore, the compound of the present invention has an advantage that the steps of manufacturing process are short, and the compound can be produced at a lower cost than conventional similar compounds. Accordingly, it is considered that the present invention can provide a low-cost anti-viral agent which has no toxicity such as bone marrow cell growth inhibition or mutagenicity and is produced in a small number of the steps of manufacturing process.

The present application claims priority from Japanese Patent Application No. 2000-54675.

What is claimed is:

1. A phosphonate nucleotide compound represented by the following formula (I) or a salt thereof, or a hydrate or solvate thereof:

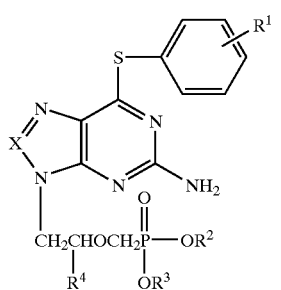

(I)

wherein,
R$^1$ is a hydroxyl group; each of R$^2$ and R$^3$ is independently a hydrogen atom, a $C_1$–$C_{22}$ alkyl group, an alkanoyloxymethyl group, an alkanoylthioethyl group, or an ethyl group substituted by one or more halogen atoms; R$^4$ is a hydrogen atom, a $C_1$–$C_4$ alkyl group, a $C_1$–$C_4$ hydroxyalkyl group, or a $C_1$–$C_4$ alkyl group substituted by one or more halogen atoms; and X is CH or a nitrogen atom.

2. The phosphonate nucleotide compound or salt thereof, or hydrate or solvate thereof according to claim 1, wherein each of R$^2$ and R$^3$ is independently a hydrogen atom, a $C_1$–$C_{22}$ alkyl group, or an ethyl group substituted by one or more halogen atoms.

3. The phosphonate nucleotide compound or salt thereof, or hydrate or solvate thereof according to claim 1, wherein each of R$^2$ and R$^3$ is independently a hydrogen atom, a $C_1$–$C_{22}$ alkyl group, or a 2,2,2-trifluoroethyl group; and R$^4$ is a hydrogen atom or a methyl group.

4. The phosphonate nucleotide compound or salt thereof, or hydrate or solvate thereof according to claim 3, which is selected from the group consisting of the following compounds:

2-amino-9-[2-(phosphonomethoxy)ethyl]-6-(4-hydroxyphenylthio)purine bis (2,2,2-trifluoroethyl) ester;
2-amino-9-[2-(phosphonomethoxy)ethyl]-6-(3-hydroxyphenylthio)purine bis (2,2,2-trifluoroethyl) ester;
2-amino-9-[2-(phosphonomethoxy)ethyl]-6-(2-hydroxyphenylthio)purine bis (2,2,2-trifluoroethyl) ester;
2-amino-9-[2-(phosphonomethoxy)propyl]-6-(4-hydroxyphenylthio)purine bis(2,2,2-trifluoroethyl) ester;
2-amino-9-[2-(phosphonomethoxy)propyl]-6-(3-hydroxyphenylthio)purine bis(2,2,2-trifluoroethyl) ester;
2-amino-9-[2-(phosphonomethoxy)propyl]-6-(2-hydroxyphenylthio)purine bis(2,2,2-trifluoroethyl) ester;
2-amino-9-[2-(phosphonomethoxy)ethyl]-6-(4-hydroxyphenylthio)purine methyl(2,2,2-trifluoroethyl) ester;
2-amino-9-[2-(phosphonomethoxy)ethyl]-6-(3-hydroxyphenylthio)purine methyl(2,2,2-trifluoroethyl) ester;
2-amino-9-[2-(phosphonomethoxy)ethyl]-6-(2-hydroxyphenylthio)purine methyl(2,2,2-trifluoroethyl) ester;
2-amino-9-[2-(phosphonomethoxy)ethyl]-6-(4-hydroxyphenylthio)purine methyl(2,2,2-trifluoroethyl) ester;
2-amino-9-[2-(phosphonomethoxy)ethyl]-6-(3-hydroxyphenylthio)purine methyl(2,2,2-trifluoroethyl) ester;
2-amino-9-[2-(phosphonomethoxy)ethyl]-6-(2-hydroxyphenylthio)purine methyl(2,2,2-trifluoroethyl) ester;
2-amino-9-[2-(phosphonomethoxy)ethyl]-6-(4-hydroxyphenylthio)purine (2,2,2-trifluoroethyl) ester;
2-amino-9-[2-(phosphonomethoxy)ethyl]-6-(3-hydroxyphenylthio)purine (2,2,2-trifluoroethyl) ester;
2-amino-9-[2-(phosphonomethoxy)ethyl]-6-(2-hydroxyphenylthio)purine (2,2,2-trifluoroethyl) ester;
2-amino-9-[2-(phosphonomethoxy)propyl]-6-(4-hydroxyphenylthio)purine (2,2,2-trifluoroethyl) ester;
2-amino-9-[2-(phosphonomethoxy)propyl]-6-(3-hydroxyphenylthio)purine (2,2,2-trifluoroethyl) ester;
2-amino-9-[2-(phosphonomethoxy)propyl]-6-(2-hydroxyphenylthio)purine (2,2,2-trifluoroethyl) ester;
2-amino-9-[2-(phosphonomethoxy)ethyl]-6-(4-hydroxyphenylthio)purine;
2-amino-9-[2-(phosphonomethoxy)ethyl]-6-(3-hydroxyphenylthio)purine;
2-amino-9-[2-(phosphonomethoxy)ethyl]-6-(2-hydroxyphenylthio)purine;
2-amino-9-[2-(phosphonomethoxy)propyl]-6-(4-hydroxyphenylthio)purine;
2-amino-9-[2-(phosphonomethoxy)propyl]-6-(3-hydroxyphenylthio)purine; and
2-amino-9-[2-(phosphonomethoxy)propyl]-6-(2-hydroxyphenylthio)purine.

5. The phosphonate nucleotide compound or salt thereof, or hydrate or solvate thereof according to claim 1, wherein each of R$^2$ and R$^3$ is a 2,2,2-trifluoroethyl group; and R$^4$ is a hydrogen atom or a methyl group.

6. The phosphonate nucleotide compound or salt thereof, or hydrate or solvate thereof according to claim 5, which is selected from the group consisting of the following compounds:

2-amino-9-[2-(phosphonomethoxy)ethyl]-6-(4-hydroxyphenylthio)purine bis (2,2,2-trifluoroethyl) ester;

2-amino-9-[2-(phosphonomethoxy)ethyl]-6-(3-hydroxyphenylthio)purine bis (2,2,2-trifluoroethyl) ester;

2-amino-9-[2-(phosphonomethoxy)ethyl]-6-(2-hydroxyphenylthio)purine bis (2,2,2-trifluoroethyl) ester;

2-amino-9-[2-(phosphonomethoxy)propyl]-6-(4-hydroxyphenylthio)purine bis(2,2,2-trifluoroethyl) ester;

2-amino-9-[2-(phosphonomethoxy)propyl]-6-(3-hydroxyphenylthio)purine bis(2,2,2-trifluoroethyl) ester;

2-amino-9-[2-(phosphonomethoxy)propyl]-6-(2-hydroxyphenylthio)purine bis(2,2,2-trifluoroethyl) ester.

7. The phosphonate nucleotide compound or salt thereof, or hydrate or solvate thereof according to claim 1, wherein each of $R^2$ and $R^3$ is a 2,2,2-trifluoroethyl group; and $R^4$ is a hydrogen atom.

8. The phosphonate nucleotide compound or salt thereof, or hydrate or solvate thereof according to claim 7, which is 2-amino-9-[2-(phosphonomethoxy)ethyl]-6-(2-hydroxyphenylthio)purine bis(2,2,2-trifluoroethyl) ester.

9. The phosphonate nucleotide compound or salt thereof, or hydrate or solvate thereof according to claim 7, which is 2-amino-9-[2-(phosphonomethoxy)ethyl]-6-(3-hydroxyphenylthio)purine bis(2,2,2-trifluoroethyl) ester.

10. The phosphonate nucleotide compound or salt thereof, or hydrate or solvate thereof according to claim 7, which is 2-amino-9-[2-(phosphonomethoxy)ethyl]-6-(4-hydroxyphenylthio)purine bis(2,2,2-trifluoroethyl) ester.

11. A pharmaceutical composition, which comprises a substance selected from the group consisting of the compound and salt thereof, and hydrate and a solvate thereof according to claim 1, and a pharmacologically acceptable pharmaceutical additive.

12. A method for treating a viral infection caused by a virus selected from the group consisting of herpes simplex virus type I, herpes simplex virus type 2 cytomegalovirus, varicella-zoster virus, and hepatitis B virus, which comprises administering a therapeutically effective amount of the compound according to claim 1 to a patient in need thereof.

13. The method according to claim 12, wherein the virus is a hepatitis B virus.

* * * * *